United States Patent [19]

Nelson

[11] 4,188,468
[45] Feb. 12, 1980

[54] PHENYL-SUBSTITUTED 5,6-DIHYDRO-PROSTACYCLIN ANALOGS

[75] Inventor: Norman A. Nelson, Galesburg, Mich.

[73] Assignee: The Upjohn Company, Kalamazoo, Mich.

[21] Appl. No.: 960,373

[22] Filed: Nov. 13, 1978

Related U.S. Application Data

[63] Continuation-in-part of Ser. No. 857,203, Dec. 5, 1977, Pat. No. 4,125,713, which is a continuation-in-part of Ser. No. 788,147, Apr. 19, 1977, abandoned, which is a continuation-in-part of Ser. No. 691,399, Jun. 1, 1976, abandoned.

[51] Int. Cl.$^2$ .......................................... C07D 307/93
[52] U.S. Cl. ................................................ 542/429
[58] Field of Search ........................................ 542/429

[56] References Cited
PUBLICATIONS

Johnson, et al., J.A.C.S., 99:12, Jun. 1977, pp. 4182–4184.

Primary Examiner—Alan L. Rotman
Assistant Examiner—Bernard Dentz
Attorney, Agent, or Firm—Morris L. Nielsen

[57] ABSTRACT

5,6-Dihydro-prostacyclin (PGI$_1$) analogs substituted with hydroxyphenyl groups, illustrated for example, by a compound of the formula

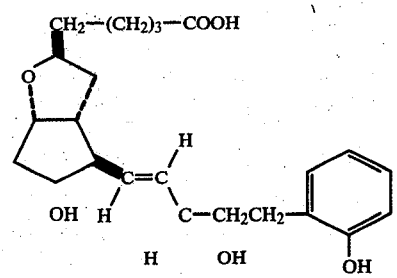

i.e. 9-deoxy-6S,9α-epoxy-17-(o-hydroxyphenyl)-18,19,20-trinor-PGF$_1$, said products having pharmacological utility.

15 Claims, No Drawings

PHENYL-SUBSTITUTED 5,6-DIHYDRO-PROSTACYCLIN ANALOGS

CROSS REFERENCE TO RELATED APPLICATIONS

This application is a continuation-in-part of copending application Ser. No. 857,203 filed Dec. 5, 1977 now U.S. Pat. 4,125,713, which was a continuation-in-part of then copending application Ser. No. 788,147 filed Apr. 19, 1977 since abandoned, which was a continuation-in-part of then copending application Ser. No. 691,399 filed June 1, 1976 and since abandoned.

BACKGROUND OF THE INVENTION

This invention relates to products having prostacyclin-like structure and to processes for preparing them. In particular this invention relates to hydroxyphenyl substituted 5,6-dihydro-prostacyclin analogs and to processes for preparing them.

Prostacyclin is an organic compound related to prostaglandins, identified as (5Z)-9-deoxy-6,9α-epoxy-Δ$^5$-PGF$_1$, and represented by the formula:

I $$\text{(structure with (CH}_2\text{)}_3\text{—COOH, C}_5\text{H}_{11}\text{, OH groups)}$$

See R.A. Johnson et al., Prostaglandins 12, 915 (1976) and J. Am. Chem. Soc. 99, 4182 (1977).

For background in the prostacyclin nomenclature see R.A. Johnson et al., Prostaglandins 15, 737 (1978).

This application is a continuation-in-part of Ser. No. 857,203 filed Dec. 5, 1977 for which the final fee has been paid following notice of allowance. The essential material for this application, including the detailed background, disclosure of the invention and utility is incorporated by reference from that application, to issue as U.S. Pat. No. 4,125,713, under the provisions of M.P.E.P. 608.01(p).

SUMMARY OF THE INVENTION

The compound of this invention are represented by the formula

II $$\text{(structure with CH}_2\text{—(CH}_2\text{)}_3\text{—COOR}_{19}\text{, Q}_7\text{, OH groups)}$$

In formula II and in other formulas hereinafter including formulas in the Charts, the terms $Q_7$, $R_{19}$, and the like are as defined in the TABLE herein.

TABLE

Definition of Terms for Formulas $Q_1$ is $$\text{R}_3\diagup\diagdown\text{OR}_{40} \text{ or } \text{R}_3\diagdown\diagup\text{OR}_{40}$$

wherein $R_3$ is hydrogen or alkyl of one to 4 carbon atoms, inclusive, and $R_{40}$ is as defined below.

$Q_7$ is $$\text{R}_3\diagup\diagdown\text{OH} \text{ or } \text{R}_3\diagdown\diagup\text{OH}$$

wherein $R_3$ is as defined for $Q_1$ above.

$R_{19}$ is
(a) alkyl of one to 12 carbon atoms, inclusive,
(b) cycloalkyl of 3 to 10 carbon atoms, inclusive,
(c) aralkyl of 7 to 12 carbon atoms, inclusive,
(d) phenyl,
(e) phenyl substituted with one, 2, or 3 chloro or alkyl of one to 4 carbon atoms, inclusive, (f) $\text{—C}_6\text{H}_4\text{—C(O)—CH}_3$ (g) $\text{—C}_6\text{H}_4\text{—NH—C(O)—C}_6\text{H}_4\text{—NH—C(O)—CH}_3$, (h) $\text{—C}_6\text{H}_4\text{—NH—C(O)—C}_6\text{H}_5$, (i) $\text{—C}_6\text{H}_4\text{—NH—C(O)—CH}_3$, (j) $\text{—C}_6\text{H}_4\text{—NH—C(O)—NH}_2$, (k) $\text{—C}_6\text{H}_4\text{—CH=N—NH—C(O)—NH}_2$, (l) 2-naphthyl, (m) $\text{—CH(R}_{35}\text{)—C(O)—R}_{34}$ wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl,
(n) hydrogen; or (o) a pharmacologically acceptable cation.

$R_{40}$ is
tetrahydropyran-2-yl, tetrahydrofuranyl, or a group of the formula

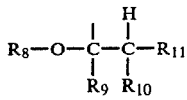

wherein $R_8$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, $-(CH_2)_a-$ or $-(CH_2)_b-O-(CH_2)_c-$ wherein "a" is 3, 4, or 5, b is one, 2, or 3, and c is one, 2, or 3 with the proviso that b plus c is 2, 3, or 4, and wherein $R_{11}$ is hydrogen or phenyl.

THP is tetrahydropyran-2-yl.

~ (wavy line) indicates attachment in alpha or beta configuration.

END OF TABLE

An example of a preferred specific compound is represented by the formula

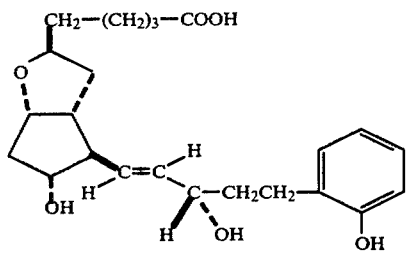

identified as 9-deoxy-6S,9α-epoxy-17-(o-hydroxyphenyl)-18,19,20-trinor-PGF$_1$, alternately "(6S)-17-(o-hydroxyphenyl)-18,19,20-trinor-PGI$_1$".

To obtain the optimum combination of biological response specificity, potency, and duration of activity, certain compounds within the scope of formula II are preferred. For example it is preferred that $Q_7$ be

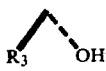

wherein it is especially preferred that $R_3$ be hydrogen or methyl.

Another preference is that the attachment of the carboxyl terminated side chain be in the 6β(6S) configuration.

Another preference, as to $-COOR_{19}$, is that $R_{19}$ be hydrogen or alkyl of one to 4 carbon atoms, especially methyl.

Another preference, as to $R_{19}$, is the p-acetylphenyl group.

Reference to Charts A and B herein will make clear the process by which some of the formula-II compounds are obtained. Chart A reviews the process for preparing certain starting materials for Chart B, i.e. the THP-blocked phenyl-substituted PGF$_{2\alpha}$-type compound of formula X within the scope of the formula-XI compounds. Background is known in the art, for example U.S. Pat. No. 3,987,087. The PREPARATION herein illustrates the preparation of compound X. Other variations are prepared by obvious methods, for example the C-15 methyl analogs by the Grignard reaction on the formula-V intermediate.

Chart B shows the steps by which compound XI is transformed to product XV. In step (a) the methyl ester is formed, for example by use of methyl iodide and an amine. In step (b) cyclization is achieved by mercuration-demercuration using techniques incorporated by reference to the predecessor parent application. In step (c) the blocking groups $R_{40}$ are replaced with hydrogen as known in the art, for example by mild acid hydrolysis. In step (d) the free acid is optionally made by saponification using potassium hydroxide in methanol-water.

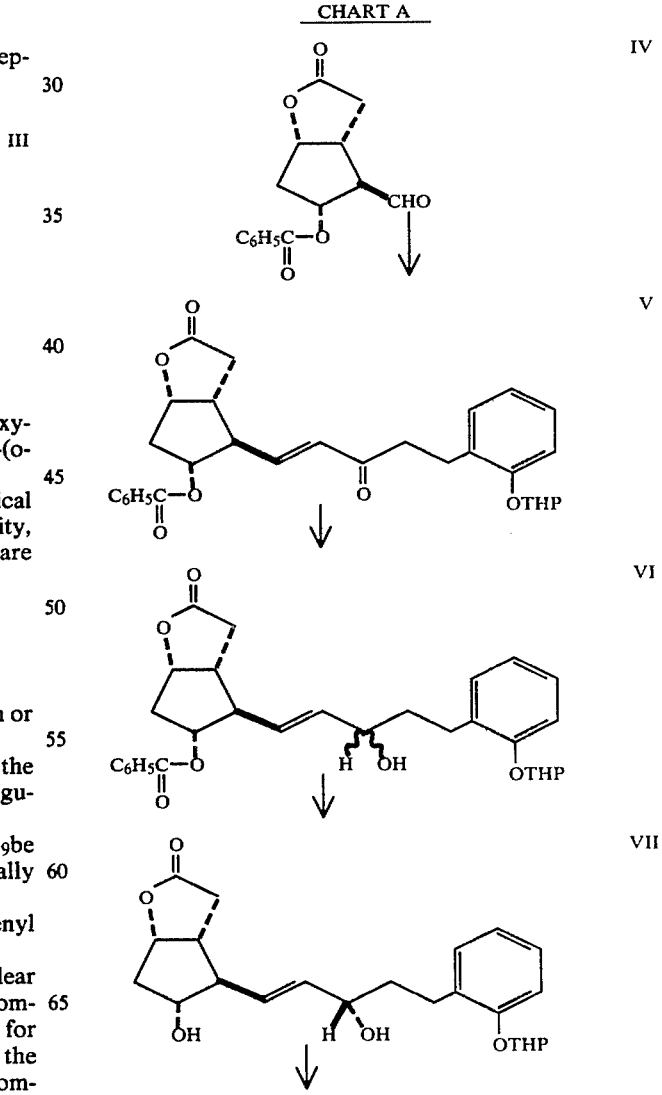

CHART A

CHART A
-continued

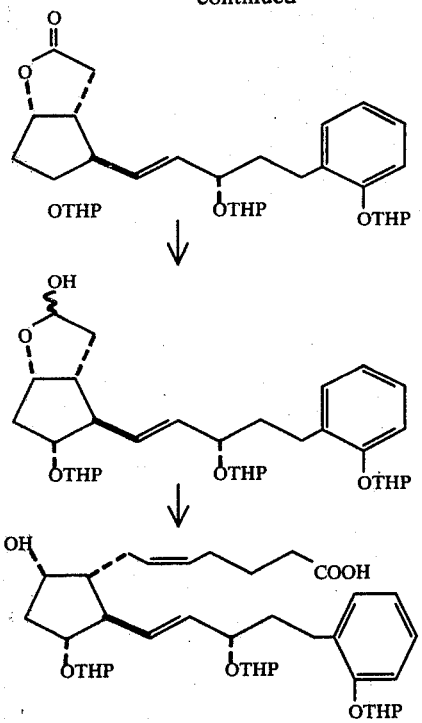

CHART B

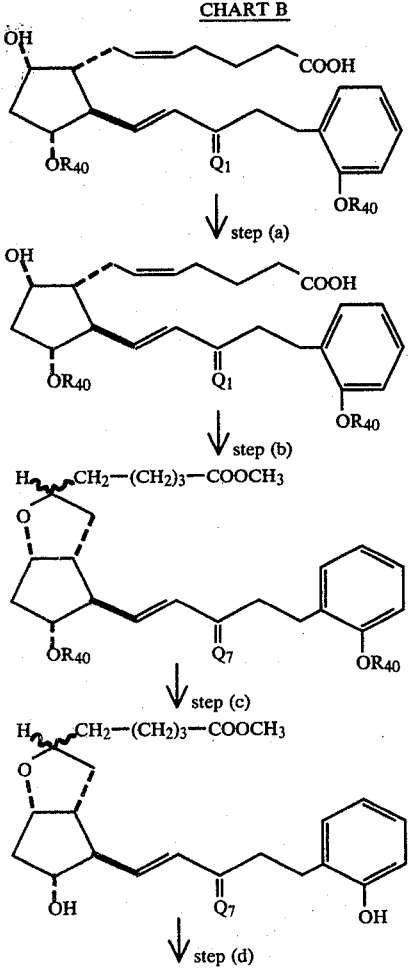

CHART B
-continued

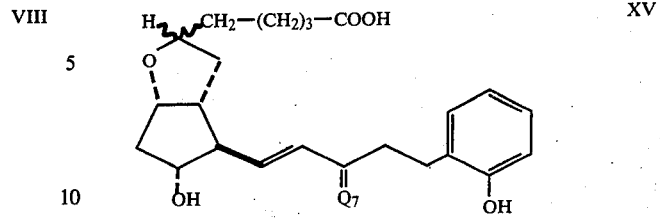

Compounds within the scope of formula II wherein $R_{19}$ is other than hydrogen or methyl including salts and other esters are prepared from the acid by methods known in the art or incorporated by reference.

DESCRIPTION OF THE PREFERRED EMBODIMENTS

The invention is further illustrated by, but not limited to, the following Preparation and Example.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60 or XL-100 spectrophotometer in deuterochloroform solutions with tetramethylsilane as an internal standard.

Mass spectra are recorded on a Varian Model MAT CH7 Mass Spectrometer, a CEC Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"Ether", herein, refers to diethyl ether.

"HPLC", herein, refers to high pressure liquid chromatography.

"Skellysolve B", herein, refers to mixed isomeric hexanes.

"THP", herein, refers to tetrahydropyran-2-yl.

"TLC", herein, refers to thin layer chromatography.

"Concentrating", as used herein, refers to concentration under reduced pressure, preferably at less than 50 mm. and at temperatures below 35° C.

"Drying", as used herein, refers to contacting a compound, in solution, with an anhydrous agent such as sodium sulfate or magnesium sulfate to remove water and filtering to remove solids.

Silica gel chromatography, as used herein, is understood to include elution, collection of fractions, and combination of those fractions shown by TLC to contain the desired product free of starting material and impurities.

PREPARATION 17-(o-Tetrahydropyranyloxyphenyl)-18,19,20-trinor-PGF$_{2\alpha}$, 11,15-bis-(Tetrahydropyranyl Ether) (Formula X)

I. Refer to Chart A. Refer to U.S. Pat. No. 3,987,087, especially column 110 for the formula-IV starting lactone aldehyde. There is first prepared the formula-V lactone corresponding 53 formula LXXVIII of Chart L of that patent at columns 60-62. Dimethyl 2-oxo-4-(o-hydroxyphenyl)-butylphosphonate, 4-tetrahydropyranyl ether (12.95 g.) in 20 ml. of tetrahydrofuran is added to sodium hydride (1.54 g. 57% dispersion in oil) in 150 ml. of tetrahydrofuran under nitrogen at about 25° and stirred for 45 min. The mixture is cooled to 0° C. and a solution of the lactone aldehyde, viz. 3α-benzoyloxy-2β-carboxaldehyde-5α-hydroxy-1α-cyclopentaneacetic acid γ-lactone, (7.67 g.) in 65 ml. of tetrahydrofuran is added. The mixture is stirred at 0° for one hr. and at 25° for 0.5 hr. The reaction is quenched with 15 ml. of glacial acetic acid and diluted with brine. The mixture is extracted with ethyl acetate and the organic phase is washed with saturated aqueous sodium bicarbonate and brine, dried, and concentrated to 17.06 g. The residue is chromatographed eluting with ethyl acetate (35–45%)-Skellysolve B, to yield the formula-IV lactone, viz. 3α-benzoyloxy-5α-hydroxy-2β-[3′-oxo-5′-(o-tetrahydropyranyloxyphenyl)-trans-1′-pentenyl]-1α-cyclopentane acetic acid, γ-lactone, 14.66 g. having NMR peaks at 1.42–3.22, 3.38–4.27, 4.87–5.57, 6.12. 6.43–7.65, and 7.87–8.15δ.

II. The formula-VI compounds are obtained by reducing the above product with sodium borohydride. The formula-V enone (14.66 g.) in 100 ml. of methanol and 10 ml. of methylene chloride is added dropwise to a stirred mixture of sodium borohydride (1.54 g.) in 150 ml. of methanol at −30° under nitrogen. After stirring for 1.5 hr. the mixture is quenched with 5 ml. of glacial acetic acid, concentrated, diluted with brine and extracted with ethyl acetate. The organic phase is washed with saturated aqueous sodium bicarbonate and brine, dried, and concentrated to 14.97 g. The residue is chromatographed eluting with ethyl acetate (55%)-hexane. From 2.51 g. charged there is obtained 1.00 g. of the 3′S formula-VI compound and 0.68 g. of the 3′R compound.

III. The formula-VII (15S) compound is obtained by removing the benzoate group with sodium methoxide. The 15S formula-VI compound (1.34 g.) in 40 ml. of methanol is treated with sodium methoxide (2.3 ml. of 25% solution in methanol) at 0° C. for 4.5 hr., thereafter at about 25° for 0.5 hr. It is cooled to 0° and quenched with 1.5 ml. of glacial acetic acid and diluted with brine-saturated aqueous sodium bicarbonate (1:1) and extracted with ethyl acetate. The organic phase is washed with saturated aqueous sodium bicarbonate and brine, dried, and concentrated to 1.43 g. of the formula-VII compound, having NMR peaks at 1.33–2.92, 3.15, 3.38–4.25, 4.80, 5.08–5.67, and 6.80–7.38δ.

IV. The formula-VIII compound is prepared from 1.43 g. of the above product in 25 ml. of methylene chloride, 30 mg. of pyridine hydrochloride, and 1.9 ml. of dihydropyran at 25° for 24 hr. After work-up there is obtained a residue of 2.25 g. The residue is chromatographed eluting with ethyl acetate (30%)-Skellysolve B, to yield the formula-VIII compound, viz. 3α, 5α-dihydroxy-2β-[3′α-hydroxy-5′-(o-tetrahydropyranyloxyphenyl)-trans-1′-pentenyl]-1α-cyclopentane acetic acid, γ-lactone, 3,3′-bis-(tetrahydropyranyl ether). 1.50 g., having NMR peaks at 0.75–2.95, 3.25–4.23, 4.60–5.17, 5.25–5.80, and 6.80–7.33δ.

V. The formula- IX lactol is obtained by reduction with diisobutylaluminum hydride. The above product (4.54 g.) in 150 ml. of toluene is treated under nitrogen with diisobutylaluminum hydride (9.0 ml. of 25% solution in toluene) added dropwise at −78° and then stirred at −78° for 0.5 hr. There is added an equal amount of diisobutylaluminum hydride and stirring continued at −78° for 0.5 hr. The reaction mixture is quenched with 20 ml. of tetrahydrofuran-water (1:1), diluted with brine and extracted with ether. The organic phase is washed with dilute (1N)aqueous sodium hydroxide and brine, dried and concentrated to the lactol, 4.94 g. The residue is chromatographed, eluting with ethyl acetate (40%)-Skellysolve B to yield 4.32 g. of the lactol, having NMR peaks at 1.23–2.98, 3.08–4.38, 4.42–4.83, 5.32–5.73, and 6.73–7.48δ.

VI. The formula-X title compound is obtained by the Wittig reaction. The ylid is prepared from 4-carboxybutyltriphenylphosphonium bromide (3.95 g.) and sodio methylsulfinylcarbanide (from 0.83 g. of sodium hydride and dimethyl sulfoxide) at 65°. To it is added the formula-IX lactol (1.14 g.) in 10 ml. of dimethyl sulfoxide dropwise at 15° and the mixture is stirred for 2 hr. The mixture is quenched with water, diluted with ether, and the organic phase extracted with 1N. aqueous sodium hydroxide. The aqueous phase is acidified to pH 2 and extracted with ether. The combined ether extracts are washed with water and brine, dried and concentrated to 1.16 g. The residue is chromatographed eluting with ethyl acetate (35%)-Skellysolve B, to yield the title compound, 0.55 g. having NMR peaks at 0.90–3.00, 3.23–4.37, 4.60–4.90, 5.12–5.93, and 6.80–7.38δ.

Replacement of the tetrahydropyranyl groups of the formula-X compound with hydrogen in the usual way yields 17-(o-hydroxyphenyl)-18,19,20-trinor-PGF$_{2\alpha}$.

EXAMPLE

9-Deoxy-6,9α-epoxy-17-(o-hydroxyphenyl)-18,19,20-trinor-PGF$_1$ (Formula XV) as its 6R and 6S isomers.

I. Refer to Chart B. There is first prepared the formula-XII methyl ester. The formula-XI compound, viz. 17-(o-tetrahydropyranyloxy-phenyl)-18,19,20-trinor-PGF$_{2\alpha}$, 11, 15-bis-(tetrahydropyranyl ether) (Preparation, 1.19 g.) is treated in 20 ml. of acetonitrile with 1.0 ml. of methyl iodide and 0.70 ml. of diisopropylethylamine at about 25° for 4 hr. There is then added additional (0.5 ml.) methyl iodide and 0.35 ml. of diisopropylethylamine and stirring continued for 2 hr. The mixture is diluted with brine and 0.5 M aqueous potassium hydrogen sulfate and extracted with ethyl acetate. The organic phase is washed with aqueous sodium bicarbonate and brine, dried, and concentrated to 1.04 g. The residue is chromatographed, eluting with ethyl acetate (35%)-hexane, to yield 0.9 g. of the methyl ester, having NMR peaks at 1.17–2.97, 3.25–4.37, 3.63, 4.60–4.92, 5.28–5.82, and 6.70–7.47δ; infrared absorption at 3460, 1735, 1600, 1590, 1490, 1455, 1440, 1355, 1320, 1220, 1200, 1180, 1120, 1080, 1040, 1020, 975 and 920 cm$^{-1}$; mass spectral peaks at 472, 295, 259, 145, and 85 and R$_f$0.44 (TLC on silica gel in ethyl acetate (50%)-Skellysolve B)).

II. Cyclization to the formula-XIII prostacyclin-type compound is done by mercuration-demercuration as set forth for similar compounds in the parent application Ser. No. 857,203 to issue as U.S. Pat. No. 4,125,713, as incorporated by reference above. The above methyl ester (0.90 g.) in 10 ml. of tetrahydrofuran is added to a mixture of mercuric acetate (0.64 g.), 15 ml. water, and 15 ml. of tetrahydrofuran, and stirred at about 25° for 1.5 hr. There is then added a solution of 0.15 g. of sodium borohydride in 3 ml. of 5% potassium hydroxide and stirring continued for 0.5 hr. The mixture is diluted with brine and extracted with ether. The organic phase is washed with brine, dried, and concentrated to 0.95 g., having NMR peaks at 1.08–3.08, 3.20–4.55, 3.63, 4.57–4.88, 5.32–5.85, and 6.75–7.38 δ; infrared absorption at 1735, 1600, 1590, 1490, 1450, 1350, 1320, 1230, 1200, 1180, 1120, 1075, 1020, 1010, 970, and 910 cm$^{-1}$; and R$_f$ 0.10 (TLC on silica gel in ethyl acetate (25%)-Skellysolve B)).

III. The blocking groups of the formula-XIII compounds are removed and the two C-6 isomers separated as follows. The above product (0.95 g.) is treated with 25 ml. of glacial acetic acid-water-tetrahydrofuran (20:10:3) and about 25° for 16 hr. The mixture is diluted with brine and extracted with ethyl acetate. The organic phase is washed with aqueous sodium bicarbonate and brine, dried and concentrated to 0.73 g. The residue is chromatographed, eluting with acetone-toluene (1:1) to yield 0.45 g. This material is again chromatographed by HPLC using Merck size B column and eluting with acetone-toluene (1:1) to yield the isomers, first the less polar 6α or 6R formula-XIV methyl ester, 0.16 g. having NMR peaks at 1.07-3.13, 3.03, 3.60, 3.53-4.35, 5.53-5.73, and 6.60-7.27 δ; infrared absorption at 3360, 1735, 1720, 1610, 1595, 1585, 1505, 1490, 1240, 1175, 1085, 1050, 970, and 755 cm$^{-1}$; mass spectral peaks at 634.3515, 619, 603, 544, 513, 454, 441, 351, 325, and 179; and R$_f$ 0.25 (TLC on silica gel in acetonitrile-toluene (1:1)). The more polar 6β or 6S formula-XIV methyl ester, 0.21 g., has essentially the same infrared and mass spectral data as above; NMR peaks at 1.08-2.98, 3.2, 3.60, 3.42-4.58, 5.55-5.80, and 6.70-7.32 δ, and 6.70-7.32 δ; and R$_f$ 0.21 (TLC on silica gel in acetonitrile-toluene (1:1)).

IV. The formula-XV acids are obtained by saponifying the corresponding formula-XIV methyl esters in a mixture of 10 ml. of 5% aqueous potassium hydroxide - 9 ml. of methanol - and 1 ml. of water at about 25° C. for 16 hr. The mixture is diluted with brine, washed with ether, and then cautiously acidified with cold 0.5 M potassium hydrogen sulfate to pH 3. The mixture is diluted with brine and extracted with ethyl acetate. The organic phase is washed with brine, dried, and concentrated. The residue is chromatographed on SilicAR®CC-4 acid-washed silica gel, eluting with ethyl acetate (50-100%)-hexane to yield the formula-XV free acid as its 6R or 6S isomer. The 6R title compound, 0.14 g., has NMR peaks at 1.05-2.93, 3.47-4.20, 5.08, 5.52-5.78, and 6.58-7.28 δ; infrared absorption at 3340, 1710, 1605, 1595, 1490, 1450, 1370, 1245, 1175, 1080, 1045, 975, and 755 cm$^{-1}$; high resolution mass spectral peak at 692.3808; and R$_f$ 0.13 (TLC on silica gel in acetone-acetic acid-methylene chloride (40:1:59). The 6S title compound, 0.15 g., has NMR peaks at 1.07-2.90, 3.40-4.60, 5.35, 5.50-5.78, and 6.58-7.30 δ, high resolution mass spectral peak at 692.3815, and infrared absorption and R$_f$ identical with the 6R isomer.

I claim:

1. A compound of the formula

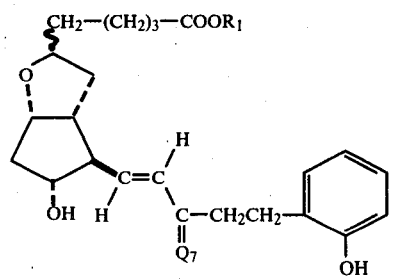

wherein Q$_7$ is

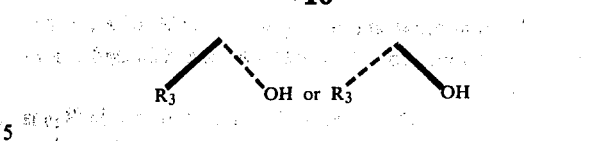

wherein R$_3$ is hydrogen or alkyl of one to 4 carbon atoms, inclusive, wherein R$_{19}$ is
- (a) alkyl of one to 12 carbon atoms, inclusive,
- (b) cycloalkyl of 3 to 10 carbon atoms, inclusive,
- (c) aralkyl of 7 to 12 carbon atoms, inclusive,
- (d) phenyl,
- (e) phenyl substituted with one, 2, or 3 chloro or alkyl of one to 4 carbon atoms, inclusive,

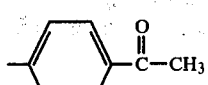 (f)

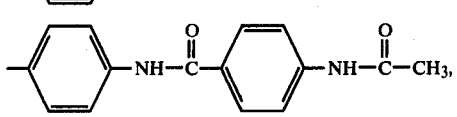 (g)

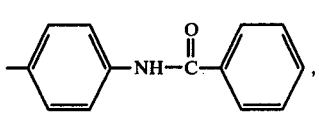 (h)

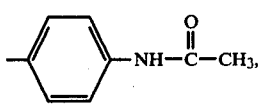 (i)

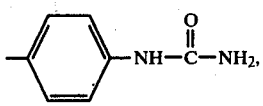 (j)

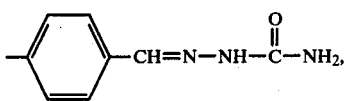 (k)

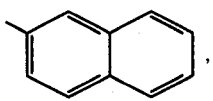 (l)

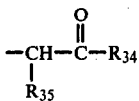 (m)

wherein R$_{34}$ is phenyl, p-bromophenyl, p-biphenylyl, p-nitrophenyl, p-benzamidophenyl, or 2-naphthyl, and wherein R$_{35}$ is hydrogen or benzoyl,
- (n) hydrogen; or
- (o) a pharmacologically acceptable cation and wherein ~ indicates attachment in alpha or beta configuration.

2. A compound according to claim 1 wherein Q$_7$ is

3. A compound according to claim 2 wherein R$_3$ is hydrogen.

4. A compound according to claim 3 wherein the carboxy-terminated side shain is attached in alpha configuration.

5. A compound according to claim 4 wherein $R_{19}$ is hydrogen or alkyl of one to 4 carbon atoms, inclusive.

6. A compound according to claim 5 wherein $R_{19}$ is methyl.

7. 9-Deoxy-(6R)-9α-epoxy-17-(o-hydroxyphenyl)-18,19,20-trinor-PGF$_1$, methyl ester, a compound according to claim 6.

8. A compound according to claim 5 wherein $R_{19}$ is hydrogen.

9. 9-Deoxy-(6R)-9α-epoxy-17-(o-hydroxyphenyl)-18,19,20-trinor-PGF$_1$, a compound according to claim 8.

10. A compound according to claim 3 wherein the carboxy-terminated side chain is attached in beta configuration.

11. A compound according to claim 10 wherein $R_{19}$ is hydrogen or alkyl of one to 4 carbon atoms, inclusive.

12. A compound according to claim 11 wherein $R_{19}$ is methyl.

13. 9-Deoxy-(6S)-9α-epoxy-17-(o-hydroxyphenyl)-18,19,20-trinor-PGF$_1$, methyl ester, a compound according to claim 12.

14. A compound according to claim 11 wherein $r_{19}$ is hydrogen.

15. 9-Deoxy-(6S)-9α-epoxy-17-(o-hydroxyphenyl)-18,19,20-trinor-PGF$_1$, a compound according to claim 14.

* * * * *

UNITED STATES PATENT OFFICE
CERTIFICATE OF CORRECTION

Patent No. 4,188,468                     Dated 12 February 1980

Inventor(s) Norman A. Nelson

It is certified that error appears in the above-identified patent and that said Letters Patent are hereby corrected as shown below:

In the Abstract, that portion of the formula reading

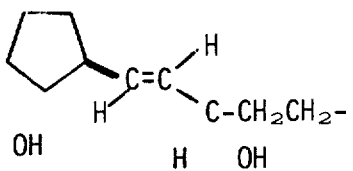      should read:      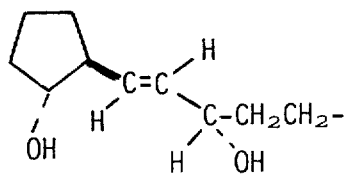

Column 5, lines 3-12, that portion of the formula reading should read:

                   

Column 5, lines 42-48, that portion of the formula reading

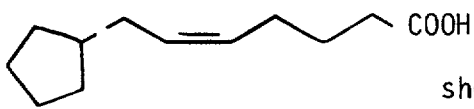                   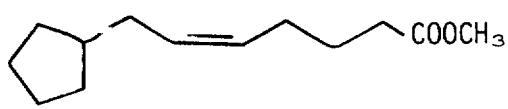

should read:

Column 5, lines 50-58, that portion of the formula reading

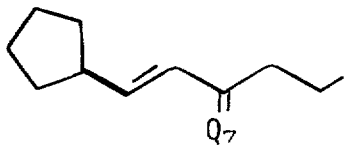      should read:      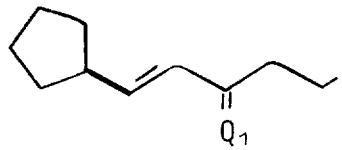

UNITED STATES PATENT OFFICE
CERTIFICATE OF CORRECTION

Patent No. 4,188,468     Dated 12 February 1980

Inventor(s) Norman A. Nelson

It is certified that error appears in the above-identified patent and that said Letters Patent are hereby corrected as shown below:

Column 9, lines 56-65, that portion of the formula reading

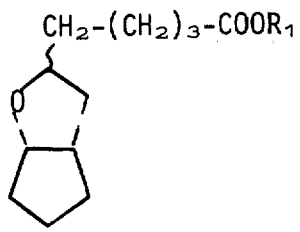    should read:    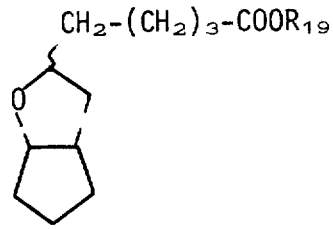

Column 11, line 2, "side shain" should read -- side chain --;
Column 12, line 11, "r$_{19}$ is" should read -- R$_{19}$ is --.

Signed and Sealed this

Tenth Day of February 1981

[SEAL]

Attest:

RENE D. TEGTMEYER

Attesting Officer     Acting Commissioner of Patents and Trademarks